United States Patent

Wu

[11] Patent Number: 5,254,720
[45] Date of Patent: Oct. 19, 1993

[54] PROCESS FOR PREPARING ARYL-SUBSTITUTED ALIPHATIC CARBOXYLIC ACIDS AND THEIR ALKYL ESTERS

[75] Inventor: Tse-Chong Wu, Baton Rouge, La.

[73] Assignee: Ethyl Corporation, Richmond, Va.

[21] Appl. No.: 996,948

[22] Filed: Dec. 28, 1992

[51] Int. Cl.$^5$ .................. C07C 69/76; C07C 51/10
[52] U.S. Cl. .................. 560/105; 562/406;
560/9; 560/20; 560/21; 560/55; 560/56; 560/100
[58] Field of Search ............ 560/105, 100, 56, 55, 560/20, 21, 9; 562/406

[56] References Cited

U.S. PATENT DOCUMENTS

| | | | |
|---|---|---|---|
| 3,632,824 | 1/1972 | Fitton et al. | 562/406 |
| 3,852,346 | 12/1974 | Forster et al. | 562/406 |
| 3,887,595 | 6/1975 | Nozaki | 562/406 |
| 3,952,034 | 4/1976 | Thompson | 260/560 |
| 4,093,592 | 6/1978 | Mayer | 560/57 |
| 4,694,100 | 9/1987 | Shimizu et al. | 560/105 |
| 4,739,109 | 4/1988 | Drent | 562/406 |
| 4,739,110 | 4/1988 | Drent | 562/406 |
| 4,786,443 | 11/1988 | Drent | 562/406 |
| 4,789,756 | 12/1988 | Drent | 562/406 |
| 5,028,576 | 7/1991 | Drent | 562/406 |
| 5,028,734 | 7/1991 | Drent | 562/406 |
| 5,081,279 | 1/1992 | Shimizu et al. | 562/406 |
| 5,087,731 | 2/1992 | Huser et al. | 562/406 |
| 5,097,061 | 3/1992 | Shimizu et al. | 562/406 |
| 5,149,868 | 9/1992 | Drent | 562/406 |

FOREIGN PATENT DOCUMENTS

| | | |
|---|---|---|
| 0055875 | 8/1986 | European Pat. Off. |
| 0106379 | 8/1986 | European Pat. Off. |
| 2114544 | 3/1971 | Fed. Rep. of Germany |
| 0119040 | 7/1982 | Japan |
| 0634587 | 3/1950 | United Kingdom |
| 0667030 | 2/1952 | United Kingdom |

OTHER PUBLICATIONS

Tsugi et al., *J. Am. Chem. Soc.*, 90(1), 94–98 (1968).
Huyser et al., *J. Org. Chem.*, 33(1), 94–99 (1968).
Bittler et al., *Angew. Chem.*, 80(9), 352–359 (1968).

Primary Examiner—Paul J. Killos
Attorney, Agent, or Firm—Richard J. Hammond

[57] ABSTRACT

A new process for preparing aryl substituted aliphatic carboxylic acids or then alkyl esters is provided. A 1-aryl substituted olefin is reacted with carbon monoxide in the presence of water or an alcohol at a temperature between about 25° C. and about 200° C. An excess of several moles of water or alcohol is preferred. An acid such as hydrochloric acid may also be added. As catalyst, a mixture of a palladium compound and a copper compound with at least one acid-stable ligand are present.

38 Claims, No Drawings

PROCESS FOR PREPARING ARYL-SUBSTITUTED ALIPHATIC CARBOXYLIC ACIDS AND THEIR ALKYL ESTERS

TECHNICAL FIELD

This invention relates to a process for preparing aryl-substituted aliphatic carboxylic acids or the esters thereof.

BACKGROUND OF THE INVENTION

Among the processes known for preparing 2-(4-isobutylphenyl)propionic acid or esters thereof is that of Shimizu et al. (U.S. Pat. No. 4,694,100, issued September, 1987), who teach the reaction of p-isobutylstyrene with carbon monoxide and water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product. The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published September, 1988), which teaches that ibuprofen can be prepared by carbonylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutylphenyl)ehtanol), a compound which is not economical to make by known processes.

Gardano et al. (U.S. Pat. No. 4,536,595, issued August, 1985) teach the preparation of alkaline salts of certain alphaarylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270-1271, discloses the alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and *J. Am. Chem. Soc.*, 112, 2803-2804 (1990).

Another process for preparing ibuprofen is that of Japanese Patent Application (Kokai) No. 59-10,545 (Mitsubishi Petrochemical, published January, 1984), which teaches that ibuprofen can be prepared by reacting p-isobutylstyrene with carbon monoxide and water or alcohol in the presence of a palladium (II) catalyst and a peroxide, e.g., cumyl hydroperoxide.

THE INVENTION

In the following specification, the meaning of the substituent groups is as follows: alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

substituted aryl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, aryloxy including phenoxy and phenoxy substituted with halo, alkyl, alkoxy and the like, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-flouoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

alkyl-substituted cycloalkyl means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl and 6-cyclohexylhexyl;

alkylthio means a divalent sulfur with alkyl occupying one of the valencies and includes the groups methylthio, ethylthio, propylthio, butylthio, pentylthio, hexylthio, octylthio and the like;

heteroaryl means 5 to 10 membered nono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl;

substituted heteroaryl means 5 to 10 membered mono- or fused-heteroaromatic ring which has at least one heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

alkanoyl means alkanoyl having 2 to 18 carbon atoms and includes, for example, acetyl, propionyl, butyryl, isobutyryl, pivaloyl, valeryl, hexanoyl, octanoyl, lauroyl and stearoyl;

aroyl means benzoyl or naphthoyl;

substituted aroyl means benzoyl or naphthoyl substituted by at least one substituent selected from the group consisting of halogen, amino, nitro, hydroxy, alkyl, alkoxy and haloalkyl on the benzene or naphthalene ring;

heteroarylcarbonyl means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl and benzimidazolylcarbonyl;

substituted heteroarylcarbonyl means the abovementioned heteroarylcarbonyl which is substituted by at least one substituent selected from the group consisting of halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl.

The present invention embraces any salts, racemates and individual optical isomers thereof of the compounds of the following formula (I) having a chiral carbon atom.

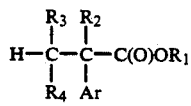

where Ar, $R_1$, $R_2$, $R_3$ and $R_4$ are subsequently defined.

The salts of the compounds of formula (I) include pharmaceutically acceptable salts such as inorganic acid addition salts (e.g. hydrochloride, hydrobromide, sulfate, nitrate or phosphate), organic acid addition salts (e.g. acetate, tartrate, citrate, fumarate, maleate, mandelate, oxalate, salicylate, hybenzate, fendizoate, methanesulfonate or p-toluenesulfonate), metallic salts (e.g. sodium salt, potassium salt, calcium salt, magnesium salt or aluminum salt), salts with bases (e.g. salt with triethylamine, diethanolamine, ammonium, guanidine, hydrazine, quinine or cinchonin) or salts with amino acids (e.g. salt with lysine or glutamine).

In accordance with the present invention, aryl-substituted aliphatic carboxylic acids or esters thereof are prepared by carbonylating an olefinic compound with carbon monoxide in a neutral or acidic medium containing at least 1 mol of water or of a $C_1$ to about $C_8$ linear or branched aliphatic alcohol per mol of olefinic compound at a temperature of between about 25° C. and about 200° C. and a carbon monoxide pressure of at least about one atmosphere in the presence of a mixture of (i) a palladium compound in which the palladium has a valence of 0-2 and (ii) a copper compound having a valence of 1 or 2 and at least one acid-stable ligand.

The olefinic compound which is carbonylated in the practice of this invention has the formula:

where Ar is unsubstituted or substituted aryl and $R_2$, $R_3$ and $R_4$ are hydrogen, alkyl, cycloalkyl, substituted or unsubstituted aryl, alkoxy, alkylthio, substituted or unsubstituted heteroaryl, alkanoyl, substituted or unsubstituted aroyl, substituted or unsubstituted heteroarylcarbonyl, trifluoromethyl or halo.

Preferably, in the compounds of formula II, Ar is unsubstituted or substituted aryl, $R_2$, $R_3$ and $R_4$ are hydrogen, $C_1$ to $C_2$ alkyl, substituted or unsubstituted phenyl or trifluoromethyl.

Most preferably Ar is phenyl substituted with alkyl or naphthyl substituted with alkoxy, $R_2$, $R_3$ and $R_4$ and are hydrogen, methyl or trifluoromethyl.

The carbonylation of the compound of formula II is conducted at a temperature between about 25° C. and about 200° C., preferably about 25°–100° C., and most preferably about 40°–80° C.. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (14.7 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from about 300 to about 3000 psig at the reaction temperature, and most preferred is a pressure from about 400 to about 800 psig.

The carbonylation is conducted in the presence of at least about one mol of water or of an aliphatic alcohol per mol of the compound of formula II; however, an excess is preferred in order to assist in driving the reaction to completion. Although there is no real upper limit to the amount of water or alcohol except that imposed by practicality (e.g. the size of the reaction vessel), an amount up to about 100 mols per mol of the compounds of formula II is useful in the process. Further, controlling the amount of water or alcohol used in the process of this invention is advantageous in terms of producing the highest yields. Therefore, an amount from about 2 to about 50 mols of water or of alcohol per mol of the compounds of formula II is preferred, and an amount from about 3 to about 24 mols of water or alcohol per mol of the such olefinic compound is most preferred. With the use of water, the free carboxylic acid of formula I is obtained; with an alcohol, the product is an carboxylic acid ester (where $R_1$ is alkyl). These compounds have the following formula:

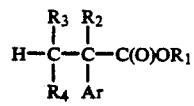

where $R_1$ is hydrogen or alkyl and Ar, $R_2$, $R_3$ and $R_4$ are as previously defined.

Any alcohol which produces an ester of the carboxylic acid may be used in the practice of this invention. In a preferred embodiment, the lower aliphatic alcohols, are used. Examples of the alcohols to be used in this embodiment include methyl alcohol, ethyl alcohol, n-propyl alcohol, isopropyl alcohol, n-, iso- sec-, and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used.

In a preferred embodiment of this invention, the carbonylation reaction is initiated under neutral conditions, i.e., with no added acid. It can also be performed in the presence of an added acid. When acids are added, such acids include sulfuric acid, phosphoric acid, sulfonic acids, or acetic or halo- substituted acetic acids. A hydrogen halide acid such as hydrochloric or hydrobromic acid is preferred. The hydrogen halide may be added as a gas phase or as a liquid phase (in the form of an alcoholic or aqueous solution); in another preferred embodiment it is added as an aqueous solution. Any aqueous concentrations may be used. Hydrochloric acid is particularly preferred, at a concentration up to about 10%; more highly preferred is a concentration from about 10% to about 30%. The amount of acid added is such as to provide up to about 40 mols of hydrogen ion per mol of olefinic compounds of formula II; more preferred is an amount to provide up to about 10 mols of hydrogen ion per mol of olefinic compound; the most preferred amount provides up to about 4 mols of hydrogen ion per mol of the compounds of formula II.

The carbonylation process of this invention is conducted in the presence of a reaction-promoting quantity of i) a mixture of a palladium compound in which the palladium has a valence of 0–2 and ii) a copper compound, with at least one acid-stable ligand. Ligands which may be used include monodentate or multidentate electron-donating substances such as those containing elements P, N, 0 and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like. In one embodiment, the palladium and copper are added as a pre-formed complex of palladium(II) chloride or bromide, copper(II) chloride or bromide and carbon monoxide or any other similar complex. In a preferred embodiment, active catalytic species are formed in situ by the addition to the reaction mixture of the individual components, i.e., a ligand, a copper compound, and a palladium compound such as the inorganic salts of palladium(II) and copper(II) such as the chlorides, bromides, nitrates, sulfates, or acetates. In the most preferred embodiment, triphenylphosphine, copper(II) chloride, and palladium(II) chloride are used and are added individually or together, either simultaneously or sequentially.

The amount of copper and palladium compounds preferably employed is such as to provide from about 4 to about 8000 mols of the compound of formula II per mol of the mixture of metal salts; more preferred is an amount to provide from about 10 to about 4000 mols of olefinic compound per mol of the salts mixture; the most preferred amounts provide from about 20 to 2000 mols of the compounds of formula II per mol of the metal salt mixture. The process of this invention is conducted in the presence of at least one mol of ligand per mol of the mixture of metal salts. More preferably about 2 to about 40 mols of ligand per mol of the mixed salts are present, and most preferably about 2 to about 20 mols of ligand per mol of mixed salts are used.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is either the corresponding ester of the carboxylic acid (if no water is present in the reaction) or a mixture of the ester and the carboxylic acid itself (if water is present). Most highly preferred are ethers, especially tetrahydrofuran. When solvents are used, the amount can be up to about 100 mL per gram of the compounds of formula II, but the process is most advantageously conducted in the presence of about 1 to 30 mL per gram of the compound of formula II.

In those embodiments of this invention in which an ester of ibuprofen is produced, the ester is converted to the acid by conventional methods of hydrolysis.

The following examples are given to illustrate the process of this invention and are not intended as a limitation thereof.

EXAMPLE 1

A) Carbon monoxide (15 ml/min) was bubbled through THF (15 mL) for 10 minutes. $PdCl_2$ (0.029 g, 0.16 mmol) and $CuCl_2$ (0.050 g, 0.37 mmol) were added. The mixture was stirred at room temperature for 3–5 hours. During this period, $PdCl_2$ and $CuCl_2$ were dissolved and a yellow solid was formed. This yellow compound can be directly used as catalyst or it can be isolate by filtering and drying under CO atmosphere. Reference: D. Zargarian and H. Alper, *Organometallics* 1991, 10, 2914.

B) The [$PdCl_2/CuCl_2$/CO] complex was freshly prepared as described above. To this catalyst (0.16 mmol) was added a solution of triphenylphosphine (0.13 g, 0.50 mmol), 4-isobutylstyrene (1.28 g, 8.0 mmol), $H_2O$ (1 mL) and THF (15 mL). The mixture was transferred to a 100-mL Hastelloy B autoclave via syringe and the autoclave was then purged with CO ($3 \times 500$ psig). The reactor was pressurized with CO (500 psig) and was agitated at 50° C. overnight (18 h). GC analysis of an aliquote found that the reaction mixture contained 96% of ibuprofen. The reactor was cooled to room temperature and CO pressure was released. Ibuprofen can be isolated as the following typical work-up procedure. Distilled $H_2O$ was added and the product was extracted with hexane. The combined hexane extracts was dried ($MgSO_4$) and was then concentrated by rotary evaporation. The resulting residue was taken with 1N NaOH and was extracted with ether. The aqueous solution was acidified with concentrated HCl. Extraction with ether, drying ($Na_2SO_4$), and evaporation afforded 2-(4-isobutylphenyl)propionic acid (ibuprofen) (1.56 g, 95% yield) as a white solid.

EXAMPLE 2

The [PdCl$_2$/CuCl$_2$/CO] complex was freshly prepared as described above. To this catalyst (0.16 mmol) was added a solution of triphenylphosphine (0.13 g, 0.50 mmol), 4-isobutylstyrene (1.28 g, 8.0 mmol), MeOH (1 mL) and THF (15 mL). The mixture was transferred to a 100-mL Hastelloy B autoclave via syringe and the autoclave was then purged with CO (3×500 psig). The reactor was pressurized with CO (500 psig) and was agitated at 50° C. overnight (18 h). GC analysis of an aliquote found that reaction gave a 96:4 mixture of methyl (b 2-(4-isobutylphenylpropionate and methyl 3-(4-isobutylphenyl)propionate in 97% conversion.

EXAMPLE 3

PdCl$_2$ (0.029 g, 0.16 mmol) and CuCl$_2$ (0.050 g, 0.37 mmol) were charged into an autoclave (Hastelloy B, 100 mL). The autoclave was purged with CO and a solution of triphenylphosphine (0.13 g, 0.50 mmol), 4-isobutylstyrene (1.28 g, 8.0 mmol), H$_2$O (1 mL) and THF (30 mL) was added. The autoclave was again purged with CO and was then filled with CO (500 psig). The autoclave was agitated at 50° C. overnight. The reactor was cooled to room temperature and CO pressure was released. GC analysis found that the reaction mixture contained 96% of ibuprofen.

EXAMPLE 4

The [PdCl$_2$/CuCl$_2$/CO] complex was freshly prepared as described above. Ph$_3$P (0.13 g, 0.50 mmol) was added and the mixture was transferred to an autoclave (Hastelloy B, 100-mL). A solution of 4-methoxystyrene (1.07 g, 8.0 mmol), H$_2$O (1 mL), and THF (15 mL) was then added via syringe. The autoclave was purged with CO (2×500 psig) and was then pressurized with CO (500 psig). After stirring at 50° C. for 16 hours, the reactor was cooled to room temperature and CO pressure was released. Standard workup afforded 2-(4-methoxyphenyl)propionic acid (1.42 g, 99% yield) Mp=52-55° C. (without further purification).

EXAMPLE 5

The [PdCl$_2$/CuCl$_2$/CO] complex was freshly prepared as described above. To this catalyst (0.16 mmol) was added a solution of triphenylphosphine (0.13 g, 0.50 mmol). The mixture was transferred to an autoclave (Hastelloy B, 100-mL). A solution of 1-decene (1.12 g, 8.0 mmol), H$_2$O (1 mL), and THF (15 mL) was then added via syringe. The autoclave was purged with CO (2×500 psig) and was then pressurized with CO (500 psig). The reactor was agitated at 50° C. overnight. GC analysis of an aliquote showed a 1:1 mixture of 2-methyldecanoic acid and n-undecanoic acid in 70% conversion. The reactor was cooled to room temperature and CO pressure was released. Standard workup yielded undecanoic acid (1.0 g, 68% yield) as an oil.

EXAMPLE 6

Pd (PPh$_3$)$_4$ (0.092 g, 0.08 mmol) and CuCl$_2$ (0.024 g, 0.18 mmol) were charged into an autoclave (Hastelloy B, 100 mL). Isobutylstyrene (0.71 g, 4.4 mmol), THF (30 mL) and H$_2$O (1 mL) were added via syringe. the autoclave was purged With CO (3×500 psig) and was then filled with CO (500 psig). After stirring at 50° C. for 19 hours, the autoclave was cooled at room temperature and CO pressure was released. GC analysis indicated ibuprofen in 86% conversion.

It is obvious that many variations may be made in the products and processes set forth above without departing from the spirit and scope of this invention.

TABLE

A Comparison of the Rates of the Catalytic Hydrocarboxylation of IBS

| Catalyst | % Conversion of Substrate to Product | | | | |
|---|---|---|---|---|---|
| | 2 h | 4 h | 6 h | 8 h | 10 h |
| [PdCl$_2$/CuCl$_2$/CO] complex (Preformed) | 27 | 50 | 70 | 84 | 95 |
| PdCl$_2$/CuCl$_2$ complex (In situ) | 20 | 38 | 52 | 69 | 84 |
| PdCl$_2$/CuCl$_2$/10% HCl | 36 | 72 | 100 | | |
| PdCl$_2$/10% HCl | 8 | 20 | 34 | 45 | 56 |
| PdCl$_2$ | 3 | 9 | 11 | 16 | 19 |

Conditions: $P_{CO}$ = 500 psig
Temperature = 50° C.
Ligand = Ph$_3$P (3 equiv)
Solvent = THF/H$_2$O (30:1)
Substrate/catalyst = 50

I claim:

1. A process for preparing an aryl-substituted aliphatic carboxylic acid or ester or salts thereof having the formula:

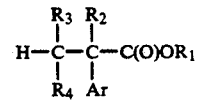

$$\begin{array}{c} R_3 \ R_2 \\ | \ \ | \\ H-C-C-C(O)OR_1 \\ | \ \ | \\ R_4 \ Ar \end{array} \quad \text{I}$$

where R$_1$ is hydrogen or alkyl, R$_2$, R$_3$ and R$_4$ are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl which comprises treating an olefinic compound of the formula:

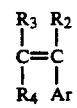

$$\begin{array}{c} R_3 \ R_2 \\ | \ \ | \\ C=C \\ | \ \ | \\ R_4 \ Ar \end{array} \quad \text{II}$$

where Ar, R$_2$, R$_3$ and R$_4$ are as previously defined and water or a compound of the formula R$_1$OH where R$_1$ is as previously defined with carbon monoxide at a pressure of at least about 1 atmosphere and a temperature from about 25° C. to about 200° C. in the absence of oxygen and in the presence of a catalyst that is i) a mixture of palladium(0) or the inorganic salts of palladium and the salts of copper and (ii) at least one acid stable ligand.

2. A process of claim 1 wherein the palladium salt is a palladium(II) salt.

3. A process of claim 2 wherein the palladium salt is palladium(II) chloride.

4. A process of claim 2 wherein the palladium salt is palladium(II) bromide.

5. A process of claim 1 wherein the ligand is a monodentate phosphine ligand.

6. A process of claim 1 wherein the ligand is a tri(hydrocarbyl)phosphine.

7. A process of claim 6 wherein the ligand is triphenylphosphine.

8. A process of claim 1 wherein the palladium salt is bis(triphenylphosphine)palladium(II) chloride or bromide and the copper salt is copper(I) chloride or copper(II) chloride.

9. A process of claim 1 wherein the amount of palladium salt and copper salt employed is such as to provide about 4-8000 mols of said olefinic compound per mol of palladium salt and copper salt.

10. A process of claim 9 wherein the palladium and copper salts and ligand are employed in amounts such as to provide about 2-20 mols of ligand per mol of palladium and copper salts in the reaction mixture.

11. A process of claim 10 wherein the palladium and copper salts and ligand are employed in amounts such as to provide about 2-12 mols of ligand per mol of palladium and copper salts in the reaction mixture.

12. A process of claim 1 wherein the carbonylation is conducted in the presence of water.

13. A process of claim 12 wherein the carbonylation is conducted in the presence of from about 2 to about 50 mols of water per mol of said olefinic compound.

14. A process of claim 13 wherein the carbonylation is conducted in the presence of from about 3 to about 24 mols of water per mol of said olefinic compound.

15. A process of claim 1 wherein the carbonylation is conducted in the presence of from about 3 to about 24 mols of methanol or ethanol per mol of said olefinic compound.

16. A process of claim 1 wherein the carbonylation is conducted in the presence of added hydrogen halide.

17. A process of claim 16 wherein the hydrogen halide is hydrogen chloride.

18. A process of claim 16 wherein the hydrogen halide is hydrogen bromide.

19. A process of claim 16 wherein the hydrogen halide is added as an aqueous solution.

20. A process of claim 19 wherein the hydrogen halide is hydrogen chloride and the concentration of the aqueous solution is a concentration up to about 30% (by weight) hydrogen chloride.

21. A process of claim 19 wherein the hydrogen halide is hydrogen chloride and the concentration of the aqueous solution is a concentration up to about 10% (by weight) hydrogen chloride.

22. A process of claim 19 wherein the amount of hydrogen halide added is an amount up to about 40 mols per mol of said olefinic compound.

23. A process of claim 1 wherein the carbonylation is conducted in a solvent.

24. A process of claim 23 wherein the solvent is a ether.

25. A process of claim 24 wherein the solvent is tetrahydrofuran.

26. A process of claim 23 wherein the solvent is methyl ethyl ketone.

27. A process of claim 1 wherein the temperature is in the range of about 25°-100° C.

28. A process of claim 1 wherein the temperature is in the range of about 40°-80° C.

29. A process of claim 27 wherein the temperature is gradually increased during the reaction.

30. A process of claim 1 wherein the carbon monoxide pressure is in the range of about 300-3000 psig.

31. A process of claim 1 wherein the carbon monoxide pressure is in the range of about 400-800 psig.

32. A process for preparing ibuprofen which comprises carbonylating 4-isobutylstyrene with carbon monoxide in an acidic medium containing tetrahydrofuran as a solvent and about 3-24 mols of water per mol of said isobutylstyrene at a temperature in the range of about 25°-100° C. and a carbon monoxide pressure in the range of about 400-800 psig in the presence of (a) a mixture of a palladium(II) compound and a copper (II) compound and (b) at least one acid-stable monodentate phosphine ligand and in the presence of an amount of hydrogen chloride such as to provide an amount up to about 10 mols of hydrogen chloride per mol of 4-isobutylstyrene.

33. A process of claim 32 wherein the palladium(II) compound is palladium(II) chloride the copper (II) compound is copper(II) chloride and the ligand is triphenylphosphine.

34. A process of claim 32 wherein the palladium, the copper, and the ligand are present in amounts such as to provide about 200-2000 mols of said isobutylstyrene per mol of the mixture of palladium and copper salts and about 2-20 mols of ligand per mol of the mixture of palladium and copper salts.

35. A process of claim 32 wherein the hydrogen chloride is added as an aqueous solution with a concentration from about 10% (by weight) to about 30% (by weight) HCl.

36. A process for preparing ibuprofen which comprises carbonylating 4-isobutylstyrene with carbon monoxide in a neutral or acidic medium containing tetrahydrofuran as a solvent and about 3-24 mols of water per mol of said isobutylstyrene and no added acid at a temperature in the range of about 40°-80° C. and a carbon monoxide pressure in the range of about 400-800 psig, in the presence of (a) a mixture of palladium(II) inorganic salt and a copper(II) inorganic salt, and (b) at least one acid-stable monodentate phosphine ligand.

37. A process of claim 36 wherein the palladium (II) salt is palladium(II) chloride and the copper salt is copper(II) chloride and the ligand is triphenylphosphine.

38. A process of claim 36 wherein the palladium and the ligand are present in amounts such as to provide about 200-2000 mols of said isobutylstyrene per mol of the mixture of palladium and copper salts.

* * * * *